United States Patent [19]

Kanda et al.

[11] Patent Number: 4,923,894
[45] Date of Patent: May 8, 1990

[54] POLYMERIC MICROPARTICLES HAVING PESTICIDAL ACTIVITY

[75] Inventors: Kazunori Kanda, Yao; Ryuzo Mizuguchi, Yawata, both of Japan

[73] Assignee: Nippon Paint Co., Ltd., Osaka, Japan

[21] Appl. No.: 849,929

[22] Filed: Apr. 9, 1986

[30] Foreign Application Priority Data

Apr. 10, 1985 [JP] Japan .................................. 60-077179

[51] Int. Cl.$^5$ .............................................. C07F 7/22
[52] U.S. Cl. ..................................... 514/493; 514/241; 514/367; 514/396; 514/461; 71/66; 71/67; 71/97; 71/DIG. 1; 106/15 R; 106/15.05
[58] Field of Search ..................... 514/493; 424/78, 81, 424/83

[56] References Cited

U.S. PATENT DOCUMENTS

| | | | |
|---|---|---|---|
| 4,039,494 | 8/1977 | Drisko | 514/493 |
| 4,075,319 | 2/1978 | Dyckman et al. | 514/493 |
| 4,468,493 | 8/1984 | Ishikura et al. | 525/123 |
| 4,512,969 | 4/1985 | Chen | 414/81 |

*Primary Examiner*—Glennon H. Hollrah
*Assistant Examiner*—Amelia A. Owens
*Attorney, Agent, or Firm*—Burns, Doane, Swecker & Mathis

[57] ABSTRACT

Polymeric microparticles having bound therewith a pesticide are disclosed. The microparticles are prepared by polymerizing a mixture of ethylenically unsaturated monomers. Active substances may be bound to the microparticles by introducing an ethylenically unsaturated function to the active substance and copolymerizing the resulting compound with the monomer mixture, or by polymerizing the monomer mixture in the presence of the active substance, or by impregnating the microparticles with a solution of the active substance.

2 Claims, No Drawings

POLYMERIC MICROPARTICLES HAVING PESTICIDAL ACTIVITY

FILED OF THE INVENTION

This invention relates to polymeric microparticles carrying a pesticidal activity. The polymeric microparticles provide a new application form of agents used for controlling various noxious and destructive animals and plants such as virucides, bacteriocides, fungicides, antiseptics, presevatives, herbicides, algicides, insecticides, acaricides, nematocides, rodenticides, repellents, sterilants and the like. They may be used in lieu of conventional application forms of such agents for protecting various industrial and other products such as coating compositions, electric wire coverings, plastic products and the like from being attacked by noxious animals and plants.

BACKGROUND OF THE INVENTION

It is well-known that various industrial and other products are damaged by the growth of microorganisms such as bacteria and fungi. Other examples of noxious animals and plants include wood-ingesting insects, aquatic animals and plants fouling ships and other marine constructions such as acorn shells and algae.

A number of agents are known and used in practice to control such noxious animals and plants. These agents are usually applied to an object to be protected as a solution or dispersion in a liquid binder, or as microcapsules incorporating an active substance in order to obtain a prolonged efficacy, although the active substance per se may be applied directly in certain cases.

Such liquid preparations have certain disadvantages in that the releasing rate of active substance is not constant and the length of the effective period is relatively short. Active substances are often not uniformily dispersed in the binder liquid or they may be susceptible to phase separation upon storage.

Microcapsules also have certain disadvantages in that they are incompatible with a liquid carrier such as organic solvents or water which swells or otherwise ruptures the capsule walls. It is generally difficult for microcapsules to control the releasing rate of an active substance in an optimum fashion. They are too large in size to form a thin film on a substrate.

It is also known that certain disinfectants such as quarternary ammonium salts or iodine based antiseptics may be adsorbed on ion exchange resins for use as a long lasting preparation. The application of this technique is limited to only ionizable active substances and the resulting preparations are not suitable for forming a film on a substrate due to their large particle sizes.

SUMMARY OF THE INVENTION

Accordingly, it is a principal object of the present invention to provide a new application form of pesticides which elimates or ameliorates the above-described disadvantages of conventional application forms. Other objects and advantages of this invention will become apparent to those skilled in the art as the description proceeds.

According to this invention, these and other objects may be accomplished by providing polymeric microparticles having bound therewith a pesticide and having a diameter of about 0.01 to 250 microns, preferably from 0.01 to 2 microns. The polymeric microparticles may be prepared by polymerizing a mixture of ethylenically unsaturated monomers.

Non-limiting examples of pesticides include virucides, bacteriocides, fungicides, antiseptics, preservatives, herbicides, algicides, insecticides, acaricides, nematocides, rodenticides, repellents, sterilants and the like.

The polymeric microparticle preparation of this invention may find uses in controlling various noxious and destructive animals and plants as conventional pesticidal preparations, but exhibit significant advantages thereover. The polymeric particles may carry an active substance in a chemically stable manner and release it at an optimum concentration for a long period of time. The polymeric microparticles may be formulated in both aqueous and nonaqueous formulations without adverse effects, and the resulting formulations may be applied even in cases where the active substances per se are not applicable for corrosion or some other reasons.

When the polymeric microparticles of this invention are incorporated in a pesticidal coating composition, they may impart not only the desired biological activity but also a structural viscosity to the composition. This improves the workability of the composition.

DETAILED DESCRIPTION OF THE INVENTION

Polymeric microparticles

Several methods are known for preparing polymeric microparticles. One method includes the steps of suspension or emulsion polymerizing a mixture of ethylenically unsaturated monomers in an aqueous medium, and removing water from the dispersion by means of solvent substitution, azeotropic distillation, centrifugation, drying and the like. Although any conventional emulsifier may be used, ampho-ionic group-containing surfactants, polymerizable monomers, oligomers and polymers are preferable. Ampho-ionic group-containing alkyd resins disclosed in U.S. Pat. No. 4,322,324 and amphoteric amino sulfonate derivatives of epoxy resins disclosed in U.S. Pat. No. 4,379,872 may advantageously be employed.

Such a method is disclosed in U.S. Pat. No. 4,530,946 assigned to the assignee of this application, the disclosure of which is incorporated herein by reference.

Another method commonly referred to as the nonaqueous dispersion (NAD) method of precipitation polymerization comprises polymerizing a mixture of ethylenically unsaturated monomers in a non-aqueous organic liquid such as aliphatic hydrocarbons or solvents having high solubility parameters in which the monomer mixture is soluble but the polymer is insoluble. Conventional suspension or bulk polymerization methods may also be employed.

The polymer microparticles used in the present invention may be prepared by any of these known methods provided that they have an average particle size of 0.01 to 250 microns for retaining good dispersibility, reactivity and stability.

Examples of ethylenically unsaturated comonomers used for the production of microparticles include methyl (meth) -acrylate, ethyl (meth)acrylate, n-butyl (meth)acrylate, isobutyl (meth)acrylate, 2-ethylhexyl (meth)acrylate, styrene, α-methylstyrene, vinyltoluene, t-butylstyrene, ethylene, propylene, vinyl acetate, vinyl propionate, acrylonitrile, methacrylonitrile, dimethyl-aminoethyl (meth) acrylate and the like. Two or more comonomers may be combined.

The starting monomer mixture preferably contains from 1 to 99% by weight of, a monomer having at least two polymerizable sites per molecule or a combination of two monomers having mutually reactive groups to give microparticles which are internally cross-linked.

Cross-linking comonomers include a monomer having at least two ethylenically unsaturated bonds per molecule and the combination of two different monomers having mutually reactive groups.

Monomers having at least two polymerization sites may typically be represented by esters of a polyhydric alcohol with an ethylenically unsaturated monocarboxylic acid, esters of an ethylenically unsaturated monoalcohol with a polycarboxylic acid and aromatic compounds having at least two vinyl substituents. Specific examples thereof include ethylene glycol diacrylate, ethylene glycol dimethacrylate, triethylene glycol dimethacrylate, tetraethylene glycol dimethacrylate, 1,3-butylene glycol dimethacrylate, trimethylolpropane triacrylate, trimethylolpropane trimethacrylate, 1,4-butanediol diacrylate, neopentyl glycol diacrylate, 1,6-hexanediol diacrylate, pentaerythritol diacrylate, pentaerythritol triacrylate, pentaerythritol tetracrylate, pentaerythritol dimethacrylate, pentaerythritol trimethacrylate, pentaerythritol tetramethacrylate, glycerol diacrylate, glycerol allyloxy dimethacrylate, 1,1,1-tris( hydroxymethyl)ethane diacrylate, 1,1,1-tris(hydroxymethyl) -ethane triacrylate, 1,1,1-tris(hydroxymethyl)ethane dimethacrylate, 1,1,1-tris(hydroxymethyl)ethane trimethacrylate, 1,1,1-tris(hydroxymethyl)-propane diacrylate, 1,1,1-tris( hydroxymethyl)propane triacrylate, 1,1,1-tris(hydroxymethyl) -propane dimethacrylate, 1,1,1-tris(hydroxymethyl)propane trimethacrylate, triallyl cyanurate, triallyl isocyanurate, triallyl trimellitate, diallyl phthalate, diallyl terephthalte and divinyl benzene.

Combinations of two monomers having mutually reactive groups may be used in place of, or in addition to monomers having two or more polymerization sites. For example, monomers having a glycidyl group such as glycidyl acrylate or methacrylate may be combined with carboxyl group-containing monomers such as acrylic, methacrylic or crotonic acid. Other examples of the combination of mutually reactive groups include amine/carbonyl, epoxide/carboxylic acid anhydride, alkyleneimine/carbonyl, amine/carboxylic acid chloride, organo-alkoxysilane/carboxyl and hydroxyl-/isocyanate.

Polymer microparticles prepared in an aqueous or nonaqueous medium may be isolated by such conventional means as filtration, spray drying, lyophilization and the like, and used directly or after milling to a suitable particle size. Alternatively, the dispersion containing the particles may be subjected to solvent substitution and the resulting dispersion may be used in a new medium.

The average size of polymer microparticles varies with the particular polymerization method. Thus, the emulsion polymerization and NAD methods are suitable for the range of 0.01 to 0.6 micron size, the precipitation polymerization method is suitable for the range of 0.2 to 2 micron size, and the suspension or bulk polymerization methods are suitable for the range of 1 to 250 microns size. The polymeric microparticles used in the present invention may be prepared by any of these known methods.

The particle size distribution of the polymer microparticles may be regulated by the selection of the polymerization method or by suitably mixing particles having different average particles sizes.

The specific density of polymer microparticles may be controlled by using an acrylic monomer containing halogen atoms or incorporating a nucleus-forming substance to the monomer mixture.

Substances having pesticidal activities

Bacteriocides and fungicides are used in a wide variety of products for industrial and household uses. Examples of such products include coating compositions, adhesives, starch products, plastics, cutting fluids, metal processing fluids, water based inks, casein, gellatin, textile, fibers, thickening agents, leather, oils and fats, paper towels, sealants, electric wires, vinyl coated steel plates, wax emulsions, rubber latex, wall paper and cloth, surfactants, shoe cream, paints, fire extinguishers, clays, glue and the like. For instance, plastic products such as films, molded products, composite materials and packaging materials made of polyurethane, epoxy, acrylic or polyvinyl chloride resin may be contaminated, deformed or otherwise deteriorated by microorganisms. Water-based coating compositions are becoming widely used in the paint industry substituting solvent type compositions. They provide nutrient sources for microorganisms and thus the incidents of fungal fouling are increasing.

Antiseptics are used in food processing, hygienic, medical and dairy fields. In the food processing field, regulations require the treatment with antiseptics not only to machines, containers, worker's hands and other objects which are directly contacted by foods, but also to ceilings, walls, floors, clothes packaging materials and other environmental installations in order to prevent secondary contamination. As the application area expands, a variety of antiseptics are used because of an increase in the number of species of contaminating microorganisms and antiseptic-resistant strains.

A number of antiseptics are known and commercially available for these purposes. Except certain antiseptics such as alcohols, aldehydes, gaseous antiseptics, inorganic chlorine compounds, iodine, hydrogen peroxide and other substances which are not suited to be carried by polymeric microparticles, any known fungicide, bacteriocide or antiseptic may be carried by polymeric microparticles of this invention. Non-limiting examples thereof include thiazole compounds such as 2-(thiocyanomethylthio)benzothiazole; phenols and halogenated phenols such as phenol, alkylphenol, bisphenol and p-chloro-m-cresol; quarternary ammonium compounds such as tetradecyl dimethyl benzylammonium chloride; triazine compounds such as hexahydro-1,3,5-triethyl-s -triazine; amphoteric surfactants such as alkyl bis-(aminoethyl)glycine; biguanide compounds such as chlorhexidine; halogen compounds such as trichloroisocyanuric acid and chloramine T; and organotin compounds such as tributyltin fluoride.

Wood products and structures are susceptible to the destruction by wood-rotting fungi and termites. Various wood preservatives are used for preventing these problems. Examples thereof include CCA (a mixture of copper, chromium and arsenic compounds), creosote oil, phenol derivatives (dinitrophenol, dinitro-o-cresol, chloronitrophenol, PCP etc.), organotin compounds, organic nitrogen compounds, organic iodine compounds, copper hydroxyquinolinate, quaternary ammonium compounds, chlordane and the like. Repellents are often used alone or in combination with other wood preservatives. The polymeric microparticles of this invention may carry these wood preservatives.

In the manufacture of cellulosic pulp and papers, slime-controlling agents and anti-fungal agents are used in the paper making step. Preservatives and anti-fungal agents are incorporated into water-based coating compositions containing binder materials such as casein, starch and latex. Preservatives and anti-fungal agents used for these purposes are generally common to those used in other fields. Examples of slime-controlling agents include chlorine compounds, chlorinated phenols, quaternary ammonium compounds, dithiocarbamate compounds, thiazole compounds, thiadiazine compounds, cyanate compounds, azide compounds, nitro compounds, halogenated acetamide compounds, organic bromine compounds, oximes and the like.

Insecticides and repellents for domestic, agricultural and horticultural uses, phytopathogenic bacteriocides and fungicides, herbicides and rodenticides may also be carried by the polymeric particles of this invention. Examples thereof include phytopathogenic bacteriocides and fungicides such as azole compounds, 2,6-dimethyl-N-acrylanilides, benzamide derivatives and carbinol compounds; insecticides such as synthetic pyrethroids, organic phosphate esters, N-methylcarbamates, insect growth regulators (IRG) such as diflubenzuron, naturally occuring substances and their derivatives; acaricides; nematocides; insect repellents; pheromones; and rodenticides such as zinc phosphide, coumarin derivatives, sodium monofluoroacetate, thallium compounds and diacin.

Examples of herbicides which may be carried by the polymeric microparticles of this invention include phenoxy compounds, diphenyl ether compounds, carbamate compounds, carboxamide compounds, urea derivatives, triazine compounds, bipyridium compounds, dinitroaniline compounds, aliphatic acid derivatives, inorganic herbicides and mixtures of these substances. Recently phytoncide found in many higher plants have become interested for its pesticidal activity. They usually occur as complexes with alkaloids, glycoside, organic acid, resins or tannic acid. Such complexes may be used as such or they may be separated into individual components by extraction. The volatility of phytoncides varies to a large extent from one to another. They exhibit varying pesticidal activities in terms of potency and spectrum. Among their selective activities of special interest are those against bacteria and other microorganisms, protozoa, insects, mollusca, aquatic animals, small land animals and plants. Terpenes such as monoterpenes, sesquiterpenes and diterpenes are known insecticides. Monoterpenes found in essential oils such as lemon oil, citronella oil, rose oil, peppermint oil, menthol oil and thymol oil are known to have an anti-microbial activity. Anti-microbial activity of vegetable plants such as allium plants, e.g. garlic and onion, mustard, carrot, cabbage and radish is also well-known. Anti-microbial activities of phytoncides have been already studied with respect to more than twenty thousand higher plants. These substances may be carried by polymeric microparticles singly or in combination with other substances.

As an important application of this invention, the polymeric particles of this invention may carry various anti-fouling substances. Such preparations may be used for protecting ships, marine constructions, fish nets, fish cages and the like from being fouled with noxious aquatic animals and plants such as acorn shells and algae.

Organic tin compounds have been widely used for this purpose as an antifouling agent. They may easily penetrate into cells and act on the mitochondria. Copper-based anti-fouling agents are also of wide use. They gradually release copper ions to inhibit the respiration of fouling animals and plants. These antifouling agents may be carried, adsorbed or otherwise incorporated by the polymeric microparticles of this invention.

The polymeric microparticles incorporating hydrolyzable monomers such as tributyltin methacrylate may be produced. These monomeric components are hydrolyzed by the action of weakly alkaline sea water to release the tin moiety. At the same time the remaining moieties are converted to free carboxyl groups which render the microparticles watersoluble. It is for this reason that the polymer microparticles of this type may be advantageously incorporated into so-called self-polishing antifouling paint to control their polishing rate in an optimum fashion. The microparticles may be combined with non-polishing film-forming vehicles to prepare a self-polishing antifouling paint.

Examples of usable antifouling agents include triorganotin compounds such as triphenyl- or tributyltin oxide, hydroxide, chloride, fluoride, acetate, fumarate, dimethyldithiocarbamate, versatate, nicotinate, $\alpha,\alpha'$-dibromosuccinate and monochloro acetate; organic lead compound such as triphenyl lead acetate and tributyl lead acetate; thiocarbamates such as zinc dimethyldithiocarbamate and tetramethylthiuram disulfide; copper compounds such as cuprous oxide, copper rohdanide, copper phosphide, copper naphthenate, copper octanate and alkylmercaptan copper methyl; metal oxides such as zinc oxide, antimony oxide, mercury oxide and arsenious anhydride; and other antifouling agents such as 2,4-dichlorophenoxyacetic acid, 2-methyl-4-chlorophenoxyacetic acid, pentachlorophenol dodecylamine salt; pentachlorophenol and triphenylborane amine.

Hydrolyzable monomers may be prepared by reacting an ethylenically unsaturated monomer having free carboxylic groups such as acrylic acid, methacrylic acid, crotonic acid, itaconic acid and its monoester, maleic acid and its monoester with a triorganotin compound such as triphenyl- or tributyltin oxide, hydroxide, halide and acetate. Also included in this class are hydrolyzable polyester oligomers having a metallized ester linkage as disclosed in Japanese Laid Open Patent Application No. 58-67722. These oligomers are hydrolyzed to release metal ions into the sea. Metals such as Cu, Zn, Cd, Hg, Sb and Pb may be bound to these oligomers.

It is well-know that ships and other marine structures suffer from damages in their maintenance by fouling with aquatic animals and plants. In order to prevent ships, fish nets and other marine structures from fouling, anti-fouling compositions containing heavy metals (e.g. copper or tin) or other toxic elements (e.g. chlorine, phosphorus or arsenic) have been widely used. However, the use of these toxic antifouling agents may present pollution of rivers, lakes or oceans. They are also undesirable from the viewpoint of public health. Substituted coumalin derivatives as disclosed in Japanese Laid Open Patent Application No. 56-40601 such as methylumbelliferon, suberosin, osthole, desmethylsuberosin, 3,3-dimethylallyumbelliferon, cedrelopsin, cumularin or pimpinellin have been found to be an antifouling agent having no such adverse effects. This is because they do not contain any heavy metal or other toxic elements.

Antifouling agents containing a lactone of the formula:

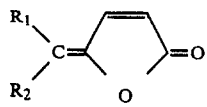

wherein $R_1$ and $R_2$ represent independently hydrogen or a $C_{1-8}$ saturated or unsaturated aliphatic hydrocarbon radical, as disclosed in Japanese Patent Application No. 54-44018 may also be carried by the polymeric microparticles according to the present invention.

Methods for incorporating active substances with polymer microparticles

One method for incorporating an active substance having pesticidal activity comprises physically absorbing or adsorbing the active substance to the polymer microparticles free of the active substance. This may be carried out by impregnating the microparticles with a solution of the active substance in a solvent in which the active substance is soluble but the microparticles are not soluble. Alternatively, the solution of active substance may be added to the suspension of polymer microparticles resulting from the polymerization step and then isolating the microparticles by the procedures as hereinbefore described.

Secondly, the active substance may be incorporated into the microparticles during their polymerization process by adding the active substance to the starting monomer mixture. This method is applicable to such an active substances that is soluble in the monomer mixture but insoluble in its polymerization medium. For example, quaternary ammonium salts also acting as surfactants may be used as an emulsifier and incorporated into the polymer microparticles when preparing the microparticles by the emulsion polymerization method. Hydrophilic active substances may be incorporated into the microparticles using the bulk polymerization method as well as the hydrolyzable oligomers disclosed in the hereinbefore cited Japanese Laid Open Patent Application No. 58-67722.

Another method comprises employing a monomer having pesticidal activity as a portion of the starting monomer mixture and polymerizing the mixture. This method may be applied, for example, to the hereinbefore described self-decaying polymer microparticles derived from triorganotin derivatives of polymerizable organic unsaturated acids. Active substances having a functional group such as an amino or hydroxyl group may be bound to the polymer microparticles by acylating the functional group with acrylic or methacrylic acid and then copolymerizing the resulting amide or ester with monomers from which the microparticles are prepared. This method is not applicable in cases where the biological activity of the active substance is lost by the acylation of such functional group. But the method may be applicable to substances having a plurality of functional groups of which partial blocking does not result in inactivation or those cases where the functional group so blocked is capable of unblocking by spontaneous hydrolysis or other chemical reactions in use.

The following examples illustrate the invention. All parts and percents therein are by weight unless otherwise indicated.

REFERENCE EXAMPLE 1

Preparation of Emulsifier

To a two liter flask having stirring means, a reflux condenser, temperature-control means, nitrogen gas-introducing tube and decanter were added 134 parts of N,N-bis(hydroxyethyl)taurine, 130 parts of neopentyl glycol, 236 parts of azelaic acid, 186 parts of phthalic anhydride, and 27 parts of xylene. The mixture was refluxed and water was removed as an azeotropic mixture with xylene. The temperature was raised to 190° C. over 2 hours and the reaction was continued with stirring until an acid number of 145 was reached.

The reaction product was cooled to 140° C. and 314 parts of CARDURA E-10(glycidyl versatate, Shell Chemical Company) was added dropwise over 30 minutes at 140° C. The reaction was continued for additional two hours with stirring. A polyester resin having an acid number of 59, a hydroxyl number of 90 and a number average molecular weight ($\overline{Mn}$) of 1054 was obtained.

REFERENCE EXAMPLE 2

Preparation of Emulsifier

A flask used in Reference Example 1 was charged with 73.5 parts of sodium taurinate, 100 parts of ethylene glycol, and 200 parts of ethylene glycol monomethyl ether. The temperature was raised to 120° C. with stirring to give a uniform solution. To the solution was added with stirring a solution of 470 parts of EPI-KOTE 1001 (Shell Chemical Company, bisphenol A diglycidyl ether epoxy resin having an epoxy equivalent of 470) in 400 parts of ethylene glycol monomethyl ether over 2 hours. The mixture was stirred at the same temperature for additional 20 hours to complete the reaction. The reaction mixture was treated as in Reference Example 1 to give 518 parts of modified epoxy resin. The resin had an acid number of 49.4 (KOH titration) and a sulfur content of 2.8% (X-ray fluorometry).

REFERENCE EXAMPLE 3

Preparation of Antifouling Varnish

A flask used in Reference Example 1 was charged with 50 parts of xylene, 30 parts of methyl isobutyl ketone and 20 parts of n-butanol. The mixture was heated to a temperature of 90° C. To this were dripped a mixture of 20 parts of tributyltin methacrylate, 60 parts of methyl methacrylate, 10 parts of methyl acrylate, 10 parts of vinyl acetate and 1.6 parts of azobisisobutyronitrile over a period of 4 hours. The mixture was maintained at the same temperature for additional 2 hours to give a varnish.

EXAMPLE 1

Microparticles Having Fungicidal Activity

A one liter flask equipped with stirring means, cooling means and temperature-control means were charged with 380 parts of deionized water, 50 parts of emulsifier prepared in Reference Example 1 and 5 parts of dimethylethanolamine. The mixture was stirred at 80° C. to make a solution.

To the solution was added a solution of 2.5 parts of azobiscyanovaleric acid and 5 parts of dimethylethanolamine in 50 parts of deionized water. Then a mixture consisting of 75 parts of methyl methacrylate, 75 parts of ethylene glycol dimethacrylate, 40 parts of styrene, 35 parts of n-butyl acrylate and 25 parts of VESTCIDE 1092 (sulfone type fungicide sold by Dainippon Ink And Chemicals, Inc.) was dripped over 90 minutes. The mixture was stirred for additional 90 minutes to give an aqueous dispersion of microparticles having a nonvolatile content of 40% and an average particle size of 52 millimicrons.

EXAMPLE 2

Microparticles Carrying Wood Preservative

A flask used in Example 1 was charged with 370 parts of deionized water, 40 parts of emulsifier prepared in Reference Example 2 and 1.5 parts of dimethylethanolamine. The mixture was stirred at 80° C. to make a solution.

To this solution was added a solution of 4.5 parts of azobiscyanovaleric acid and 4 parts of dimethylethanolamine in 45 parts of deionized water. Then a mixture consisting of 30 parts of styrene, 60 parts of methyl methacrylate, 10 parts of 2-hydroxyethyl acrylate, 10 parts of pentachlorophenyl methacrylate, 30 parts of divinylbenzene and 10 parts of p-chloro-m-xylenol was dripped over 60 minutes. Then a solution of 1.5 parts of azobiscyanovaleric acid and 1.0 parts of dimethylethanolamine in 15 parts of deionized water was added. The mixture was stirred at 80° C. for 60 minutes to give an aqueous dispersion of microparticles having a nonvolatile content of 35% and an average particle size of 62 millimicrons.

EXAMPLE 3

Anti-Fungal Microparticles

A flask used in Example 1 was charged with 400 parts of deinoized water and 4 parts of benzalkonium chloride. The flask was purged with $N_2$ gas and the content was heated to 80° C.

Then 90 % of solution of 3 parts of potassium persulfate and 1 part of sodium hydrogen sulfite in 100 parts of deionized water (solution A) was added. Next a mixture consisting of 80 parts of styrene, 140 parts of methyl methacrylate, 10 parts of ethylene glycol dimethacrylate, 140 parts of n-butyl acrylate, 10 parts of 2-hydroxyethyl methacrylate and 10 parts of bis-(tributyltin) oxide, and a solution of 1 part of 1-(3-sulfopropyl)-2-vinylpyridinium betain in 100 parts of deionized water were dripped over 1 hour, respectively. The stirring was continued for 1 hour and then the remainder of the above solution A was added. The reaction was continued for additional 2 hours to give an aqueous dispersion of polymer microparticles having a nonvolatile content of 39% and an average particle size of 0.28 microns.

EXAMPLE 4

Microparticles Having Antifouling Activity

A flask used in Example 1 were charged with 900 parts of isopropanol. The flask was purged with $N_2$ gas while heating to 50° C. To the flask was added dropwise a mixture consisting of 15 parts of tributyltin methacrylate, 7 parts of methyl methacrylate and 25 parts of ethylene glycol dimethacrylate. The mixture was then stirred for 10 minutes. After adding 1 parts of azobisisobutyronitrile, the mixture was gradually heated to 70° C. and allowed to react for 4 hours whereupon white polymer microparticles precipitated out. These particles were filtered off, washed with isopropanol three times and then dried in vacuo to obtain self-decaying polymer microparticles having antifouling activity. The average primary particle size was determined as being 2 microns by the scanning electron micrograph.

EXAMPLE 5

Microparticles Having Insecticidal Activity

A flask used in Example 1 were charged with 1000 parts of deionized water, 20 parts of polyvinyl alcohol having an average molecular weight of 1,500, 10 parts of sodium dodecylbenzenesulfonate and 10 parts of an aqueous solution of colloidal silica (LUDOX AM sold by E. I du Pont de Nemours & Co., Inc.). The mixture was heated to 60° C. under nitrogen gas stream with stirring at 1,000 rpm.

Then a mixture consisting of 5 parts of styrene, 15 parts of methyl methacrylate, 10 parts of n-butyl acrylate, 5 parts of acrylonitrile, 10 parts of ethylene glycol dimethacrylate, 5 parts of ethyl dimethyldithiophosphorylphenylacetate and 1 part of 2,2'-azobis-(2,4-dimethylvaleronitrile) was dripped over 1 hour. Thereafter the mixture was allowed to reacted at 70° C. for 5 hours to give a suspension of polymer microparticles. Then the microparticles were collected by centrifugation and washed with deionized water three times. Polymer microparticles having insecticidal activity and an average particle size of 52 microns were obtained.

EXAMPLE 6

Microparticles Having Anti-Fungal Activity

A flask used in Example 1 containing 500 parts of deionized water was heated to 75° C. Then a mixture consisting of 45 parts of 2-acrylamido-2-methylpropanesulfonic acid, 5 parts of ethylene glycol dimethacrylate, 2 parts of ELEMINOL JS-2 (polymerizable surfactant sold by Sanyo Chemical Industries, Ltd.), 5 parts of KOATCIDE (water-soluble benzimidazole based fungicide sold by Takeda Chemical Industries, Ltd.), 100 parts of deionized water and 2 parts of ammonium persulfate was dripped over 2 hours.

The mixture was allowed to stand for an additional 1 hour whereupon a polymer mass precipitated out. The precipitates were filtered off, washed with acetone, dried in vacuo, crushed and sieved to obtain polymer powder having fungicidal activity and an average particle size of 200 microns.

EXAMPLE 7

To 100 parts of commercially available white emulsion paint was added 20 parts of aqueous dispersion of microparticles prepared in Example 1. The resulting composition was applied on a filter paper (5 cm×5 cm) to a dry film thickness of 25 microns. This composition was capable of being applied at a dry film thickness of 56 microns on an aluminium substrate without running by a single coating operation.

The coated paper was dried at room temperature for 7 days and subjected to accelerated weathering in Weather-O-Meter for 500 hours.

The weathered specimen was then tested on its anti-fungal activity by the method according to JIS-Z-2911. The specimen was placed on a standard agar medium, innoculated with a spore mixture of Aspergillus niger, Penicillium citrinum and Cladosporium herbarum and cultured at 28° C. for 4 weeks. No growth of fungi was observed on the 14th day. Growth was seen in less than ⅛ area on the 28th day indicating a long lasting activity.

COMPARATIVE EXAMPLE 1

The procedure of Example 7 was repeated except that the anti-fugal microparticles prepared in Example 1 were replaced by the fungicide used therein at the same active substance level. The maximum film thickness free of running of this composition was 35 microns.

A similar anti-fungal test was carried out on the specimen coated with this composition. Growth of innoculated fungi was seen in ⅛ the area on the 14th day and in half area on the 28th day.

EXAMPLE 8

10 parts of aqueous dispersion of polymer microparticles prepared in Example 2 were thoroughly admixed with 100 parts of commercially available vinyl acetate-/ethylene based emulsion paint (nonvolatile content 45 %, lowest drying temperature 5° C.). Pine timber was coated with the resulting composition and placed in outdoor humid environment for 6 months. Destruction by wood-rotting fungi was not observed.

COMPARATIVE EXAMPLE 2

The procedure of Example 8 was repeated except that the microparticles prepared in Example 2 were replaced by p-chloro-m-xylenol in unbound form at the same active substance level. Rotting was observed after 6 months on the surfaces of timber.

EXAMPLE 9

Aqueous dispersion of polymer microparticles prepared in Example 3 was diluted tenfold with deionized water. This dilution was applied on a printed circuit board (5 cm × 5 cm) to a dry film thickness of 2 microns and dried at 80° C. for 5 minutes.

The resulting circuit board was tested for antifungal activity by the method according to JIS-Z-2911 as in Example 7. No growth of innoculated fungi was observed on the 14th day.

EXAMPLE 10

45 parts of antifouling varnish prepared in Reference Example 3, 25 parts of copper rhodanide, 15 parts of polymer powder prepared in Example 4 and 15 parts of xylene were thoroughly mixed to obtain an antifouling coating composition.

This composition was applied on a test panel to a dry film thickness of 100 microns and tested on its antifouling activity by immersing the plate in the sea near Tamano-shi, Japan. Fouling with aquatic plants and animals was not observed after 3 months and after 6 months of immersion.

The polishing rate of the coating film of this composition was determined by attaching the above plate to a disc rotor and revolving the plate in the sea water (temperature 18° to 23° C.) at a constant speed (peripheral linear speed about 35 knots) for consecutive 60 days. The polishing rate was calculated by the following equation.

$$\text{Polishing rate} = \frac{\text{initial film thickness} - \text{final film thickness}}{\text{initial film thickness}}$$

A value of 0.12 was obtained.

The composition obtained in this example thus exhibited not only antifouling activity but also a selfpolishing effect.

COMPARATIVE EXAMPLE 3

The procedure of Example 10 was repeated except that the polymer microparticles prepared in Example 4 were not added.

The test plate coated with this composition was fouled in area of 5% and 15% after 3 months and 6 months of immersion in the sea, respectively.

The polishing rate in the sea water was less than 0.01.

EXAMPLE 11

Anti-bacterial Microparticles

The procedure of Example 5 was repeated except that 5 parts of ethyl dimethyldithiophosphorylphenylacetate was replaced by 3 parts of rose oil and 2 parts of menthol oil. Polymer microparticles of average particle size of 73 microns having anti-bacterial activity were obtained.

What is claimed is:

1. Fungicide-loaded internally cross-linked polymeric microparticles having a diameter of about 0.01 to 2 microns, said microparticles being prepared by polymerizing a mixture of ethylenically unsaturated monomers wherein at least a portion of the monomer mixture is a monomer having at least two polymerizable sites per molecule or a combination of two monomers having mutually reactive groups, said monomer mixture further containing a fungicide dissolved therein, wherein said fungicide is soluble in said monomer mixture but insoluble in the polymerization medium thereof, and whereby said fungicide is physically entrapped within a polymer matrix constituting said polymer microparticles.

2. The polymeric microparticles according to claim 1, wherein said polymeric microparticles are prepared by polymerizing said monomer mixture by emulsion, non-aqueous dispersion, precipitation or suspension polymerization method.

* * * * *